United States Patent [19]
Chang et al.

[11] Patent Number: 5,581,036
[45] Date of Patent: Dec. 3, 1996

[54] BANDWIDTH SAMPLING TECHNIQUE FOR DIGITAL FOCUSING IN ARRAY IMAGING SYSTEMS

[75] Inventors: Seong H. Chang; Song B. Park, both of Seoul, Rep. of Korea

[73] Assignee: Medison Co., Ltd., Kangwon-do, Rep. of Korea

[21] Appl. No.: 367,281

[22] PCT Filed: May 23, 1994

[86] PCT No.: PCT/KR94/00055

§ 371 Date: Mar. 13, 1995

§ 102(e) Date: Mar. 13, 1995

[87] PCT Pub. No.: WO94/28467

PCT Pub. Date: Dec. 8, 1994

[30] Foreign Application Priority Data

May 24, 1993 [KR] Rep. of Korea .................. 93-8944

[51] Int. Cl.$^6$ ................ G01N 29/00; A61B 8/00
[52] U.S. Cl. ............ 73/602; 73/625; 128/661.01; 367/125; 367/126
[58] Field of Search ............... 73/625, 626, 602; 128/661.01; 367/7, 124, 125, 126

[56] References Cited

U.S. PATENT DOCUMENTS

| | | | |
|---|---|---|---|
| 4,241,610 | 12/1980 | Anderson | 73/626 |
| 4,324,258 | 4/1982 | Huebscher et al. | 128/663 |
| 4,458,533 | 7/1984 | Borburgh | 73/625 |
| 4,553,437 | 11/1985 | Luthra et al. | 73/602 |
| 4,632,124 | 12/1986 | Hiller et al. | 128/660 |
| 4,679,176 | 7/1987 | Ogawa et al. | 73/626 |
| 4,688,045 | 8/1987 | Knudsen | 342/377 |
| 4,837,578 | 6/1989 | Gammell | 73/626 |
| 4,974,211 | 11/1990 | Corl | 73/626 |
| 5,005,419 | 4/1991 | O'Donnell et al. | 73/626 |
| 5,042,303 | 8/1991 | Geluk et al. | 73/602 |
| 5,103,427 | 4/1992 | Erdol et al. | 367/7 |
| 5,197,037 | 3/1993 | Leavitt | 73/625 |
| 5,203,336 | 4/1993 | Iida et al. | 128/661.01 |
| 5,235,857 | 8/1993 | Anderson | 73/625 |
| 5,235,983 | 8/1993 | Iida et al. | 128/661.01 |

FOREIGN PATENT DOCUMENTS

| | | |
|---|---|---|
| 110621 | 6/1984 | European Pat. Off. |
| 3830729 | 3/1990 | Germany . |
| 2127992 | 4/1984 | United Kingdom . |
| 2176356 | 12/1986 | United Kingdom . |
| 2222486 | 3/1990 | United Kingdom . |
| 9113369 | 9/1991 | WIPO . |

OTHER PUBLICATIONS

M. H. Lee and S. B. Park, "New Continuous Dynamic Focusing Technique In Ultrasound Imaging" Electronics Letters, vol. 21, No. 17, pp. 749–751, Aug. 1985.
J. H. Kim, T. K. Song, and S. B. Park, "Pipelined Sampled Delay Focusing In Ultrasound Imaging Systems", Ultrasonic Imaging, vol. 9, No. 2, pp. 75–91, Apr. 1987.

*Primary Examiner*—Hezron E. Williams
*Assistant Examiner*—Richard A. Moller
*Attorney, Agent, or Firm*—Morgan & Finnegan LLP

[57] ABSTRACT

The present invention relates to an ultrasonic array imaging system for focusing ultrasonic signals which are reflected from an object to be imaged and received by an array transducer. A digital focusing method and system in accordance with the present invention compensates for phase errors which are contained in digital data by using a quadrature sampling method in digital-processing and focusing of ultrasonic signals. Each of a plurality of delayed-time eliminators receive signals generated by quadrature sampling and removes delayed-time differences from signals. Each of phase compensators receives a digital signal in which a delayed-time difference is removed, and compensates the received digital signal for phase errors. An envelope detector is used to detect an envelope signal using the phase error compensated date.

8 Claims, 4 Drawing Sheets

BANDWIDTH SAMPLING TECHNIQUE FOR DIGITAL FOCUSING IN ARRAY IMAGING SYSTEMS

BACKGROUND OF THE INVENTION

1. Field of the Invention

The present invention relates to an array imaging system, and more particularly to an ultrasonic array imaging system in which ultrasonic echoes reflected from an object to be imaged and received by an array transducer are focused in a digital fashion by applying a bandwidth sampling technique. Such an ultrasonic system can be utilized in medical diagnosis, non-destruction inspection, underwater investigation, etc. Moreover, the present invention can be applied to imaging systems using any type of array transducers including linear, phased, convex, concave and annular arrays. The present invention can be applied not only to ultrasonic imaging systems but also to radar systems using array transducers for the beam forming purpose. The present invention can be applied to any imaging modality in which the analytic signal can be effectively utilized, including B, C and M mode images, for flow measurement, phase aberration correction, tissue characterization, etc.

2. Description of the Related Art

Generally, in an ultrasonic imaging system, an ultrasonic pulse signal is transmitted toward an object to be imaged, reflected from a surface of an acoustic impedance discontinuity of the object, and received by an array transducer. The received signals are then converted into electric signals which are displayed on a video monitor after various processing. The resulting image conveys some information of the characteristics of the object being examined. In this case, the use of a short pulse increases the signal resolution and the use of an array obtains focusing capability to improve lateral resolution. In the past, various methods have been used to improve the resolution, in particular, the lateral resolution.

FIG. 1 is a schematic block diagram of a conventional ultrasonic imaging system. An ultrasonic pulse signal generated from a pulse generator 11 is supplied to an array transducer 10 via switch 12. The array transducer 10 converts an electric pulse signal into an ultrasonic signal and provides the converted signal to an object 13 to be imaged. Then, the ultrasonic signal is reflected from an acoustic impedance discontinuous surface of the object 13 and the reflected signal is again received by the array transducer 10. At this time, in a case where there are a plurality of acoustic impedance discontinuous surfaces, the ultrasonic signal is in turn reflected from each of discontinuous surfaces and is supplied to a number of transducer elements. The array transducer 10 is composed of a plurality of transducer elements. The ultrasonic signal supplied to the array transducer 10 is converted by transducer elements into an electric signal a with magnitude proportional to an intensity of the ultrasonic signal. The electric signal is amplified to the predetermined magnitude in an amplifier 14 via switch 12, processed to a video signal in a signal processor 15, and transmitted to a cathod ray tube (CRT) 16.

In such an ultrasonic imaging system, the array transducer of a probe is composed of a plurality of transducer elements in the array form. This array form improves the resolution of a picture to be displayed with focusing an ultrasonic signal. Ultrasonic signals, which are reflected from the object and supplied to the array transducer, reach the transducer elements at different times according to the positions of the respective transducer elements. That is, the farther their positions are from the middle of the array transducer 10, the amount of time necessary to reach the transducer elements increases. Even if signal focusing can be performed at a transmission focusing step of transmitting the ultrasonic signal from the array transducer 10 to the object, it is preferred that signal focusing occur at a receiving focusing step, capable of dynamic focusing, rather than the former step. In receiving focusing, differences between reach times should be respectively compensated after delayed, they are so as to focus electric signals output from the transducer elements.

FIG. 2 illustrates one embodiment of a conventional receiving focusing device of an ultrasonic signal. The device of FIG. 2 utilizes analog delayers. An array transducer 20 is composed, of n transducer elements in numbers, in which receiving signals converted into electric signals by each of transducer elements are supplied to n delayers DLY1~DLYn, respectively. Among ultrasonic signals reflected from an object and supplied to the array transducer 20, each of delayers DLY1~DLYn allows the longest delay time to an input signal of the middle transducer element with the shortest reach time and permits the shortest delay time to input signals of first and n transducer elements with the longest reach time. Therefore, the delayers DLY1~DLYn simultaneously output the delayed signals therein to an adder 22. The signals output from the respective delayers are added in the adder 22 and outputted as a focusing signal. The conventional device of FIG. 2 connects the delayers, having a predetermined delay time value, to output terminals of each of transducer elements and delays the output signal from the transducer elements. Thus, each of delayers DLY1~DLYn compensates for differences of reach time to the transducer elements of the ultrasonic signals reflected from the object. An output signal from the adder 22 is supplied to an envelope detector 23. However, in order to reduce errors during compensating of delay time, the conventional device of FIG. 2 employs a plurality of taps in the delayers. As such, such a device requires complicated hardware. Also, in the case of dynamic focusing, the delay time of each delayer should be changed. Accordingly, the more the number of focal points increases, the more complicated the hardware becomes. Moreover, impedance mismatching causes a reduction of the range dynamic focusing and a decrease of resolution therefrom.

FIG. 3 illustrates another embodiment of a conventional receiving focusing device of an ultrasonic signal. The device of FIG. 3 utilizing what is called pipelined sampled delay focusing (PSDF). In the device of FIG. 3, an array transducer 30 is composed of n transducer elements in numbers. Received ultrasonic signals are converted into electric signals by each of transducer elements. The electric signals output from transducer elements of the array transducer 30 are respectively supplied to n analog to digital converters A/D1~A/Dn of an analog to digital converting unit 31. A clock generator 32 generates sampling clocks of a frequency "fs". The A/D converting unit 31 converts each of electric signals which are input from the transducer elements according to the sampling clock into digital signals, and supplies the converted signal to memories FIFO1~FIFOn, respectively. The sampling clock of the clock generator 32 is not a uniform clock, but a variable sampling clock. That is, in the case of the dynamic focusing, the reach time of the ultrasonic signal is different from each other according to positions of each focal point. Output terminals of the A/D converting unit 31 are connected to a memory unit 33 composed of first-in-first-out memories FIFO1~FIFOn. Output data of the A/D converting unit 31 is arranged within the memory unit 33, to be output in input order. Therefore, the ultrasonic signals, which are reflected from a particular focal point and supplied to transducer elements, can be simultaneously output from the memory unit 33. After initial data corresponding to a specific focal point is supplied to the memory unit 33 and a maximum delay time goes by, data is simultaneously output from the memory unit 33. The output data is added in an adder 34, and then dynamic focusing is performed. The focused ultrasonic signal is converted into an analog signal by digital-to-analog converter 35 and the converted signal is supplied to an envelope detector 36. The envelope detector 36 detects an envelope from the input signal, and an analog-to-digital converter 37 converts the detected envelope into a digital signal.

Using such a technique, it is advantageous that the conventional device can obtain the best resolution by focusing an ultrasonic signal on all focal points requiring the dynamic focusing. However, it is disadvantageous that the level of a sampling frequency becomes high because the A/D converting unit 31 samples a radio frequency signal. For instance, in the case of an array transducer of 3.5 MHz, a sampling frequency is required beyond 28 MHz. Therefore, such a of system suffers from the problem of noise due to high sampling frequencies of A/D conversion. Furthermore, a problem with relatively expensive costs is encountered because both memories and peripheral circuits with a high speed device should be employed. In addition, since a final signal required in an ultrasonic video device is an envelope of a focused RF signal, not the focused RF signal, the detection of the envelope should be executed. However, it is difficult to detect the envelope from digital data which is sampled to a high frequency beyond 28 MHz. So, as shown in FIG. 3 the envelope detection should be executed after converting the focused digital RF data into analog data again. Accordingly, new noise may occur in a process of D/A conversion.

SUMMARY OF THE INVENTION

In order to solve the above problems, the present invention lowers the frequency band of output signals from transducer elements using bandwidth sampling methods. Signals a with low frequency band are converted into digital signals by A/D conversion using a sampling frequency beyond the bandwidth. The converted digital signals are focused through memory, and then envelope data of each of focal points is detected by an envelope detector. Embodiments of the present invention disclose both an analytic signal sampling using the Hilbert transform of the bandwidth sampling methods and a quadrature sampling. A quadrature sampling method discloses the compensation of phase errors. To accomplish the above object of the present invention, there is provided an ultrasonic imaging system which focuses reflected and received ultrasonic signals, on at least one focal point according to a receiving focusing method, the system comprising:

a plurality of transducer elements for respectively receiving the ultrasonic signals relating to a focal point and generating analog signals corresponding to the ultrasonic signals; a plurality of band transformers, coupled to each of the transducer elements, for respectively transforming each of frequency band of the input analog signals; numbers of delayed-time difference eliminators, coupled to the band transformers, for eliminating the difference of delayed times caused from positions of a focal point being between band-transformed signals and for performing analog to digital conversion; a plurality of memories, connected to each of delayed-time difference eliminators, for storing the digital signals output from the delayed-time difference eliminators; adding means for adding the output signals from the memories; and an envelope detector for detecting envelope data from output signals of the adding means.

DETAILED DESCRIPTION OF THE PREFERRED EMBODIMENTS

The preferred embodiment of the present invention will be described in detail with reference to the accompanying drawings.

Figure 4:
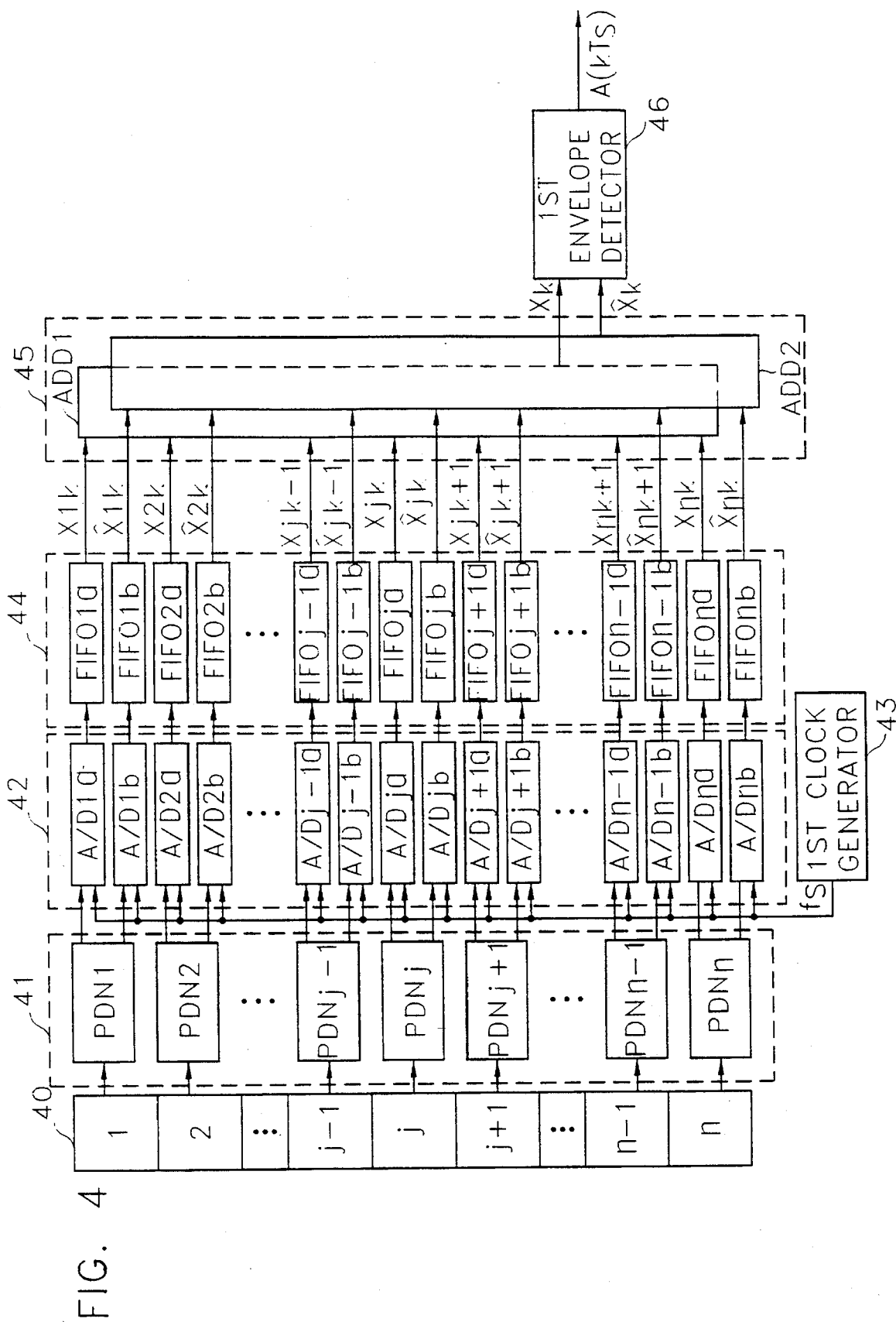
FIG. 4 is a block diagram illustrating one preferred embodiment of an ultrasonic imaging system for focusing a digital signal in accordance with the present invention.

FIG. 4 illustrates one preferred embodiment of an ultrasonic imaging system for focusing a digital signal in accordance with the present invention.

Referring to the system of FIG. 4, an array transducer 40 is composed of n transducer elements in numbers. Each of output terminals of the transducer elements is connected to each of input terminals of phase transformers PDN1~PDNn within a band transformer 41. Each of output terminals of the band transformer 41 is connected to input terminals of an analog to digital converting unit 42, respectively. The A/D converting unit 42 receives sampling frequencies $f_s$ from a first clock generator 43 and converts the received signal into a digital signal, and then the digital signal is stored in a memory unit 44. The A/D converting unit 42 and the first clock generator 43 form a delayed-time difference eliminator which compensates for the differences of any delay time between a plurality of ultrasonic signals relating to a particular focal point. The memory unit 44 simultaneously outputs the stored data to an adding unit 45. The adding unit 45 includes first and second adders 46 and 47. An envelope detector 48, coupled to outputs of the first and second adder 46 and 47, detects an envelope of the focused signal.

Figure 1:
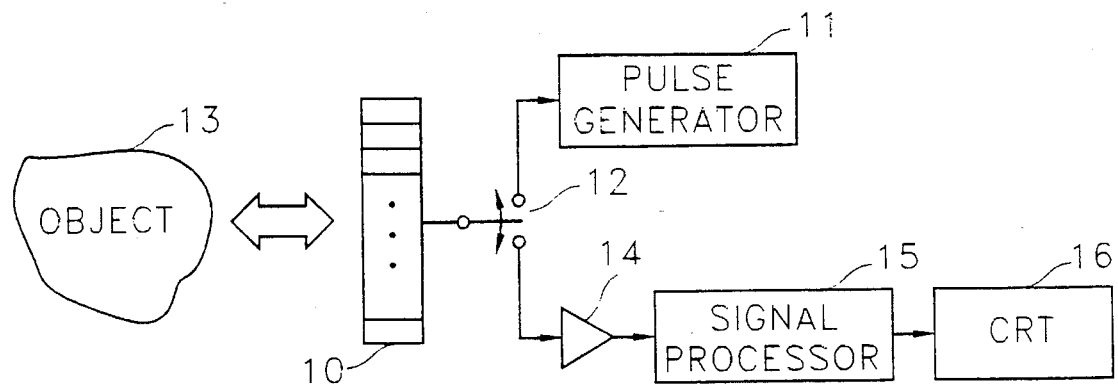
FIG. 1 is a schematic block diagram of a conventional ultrasonic imaging system.
Figure 2:
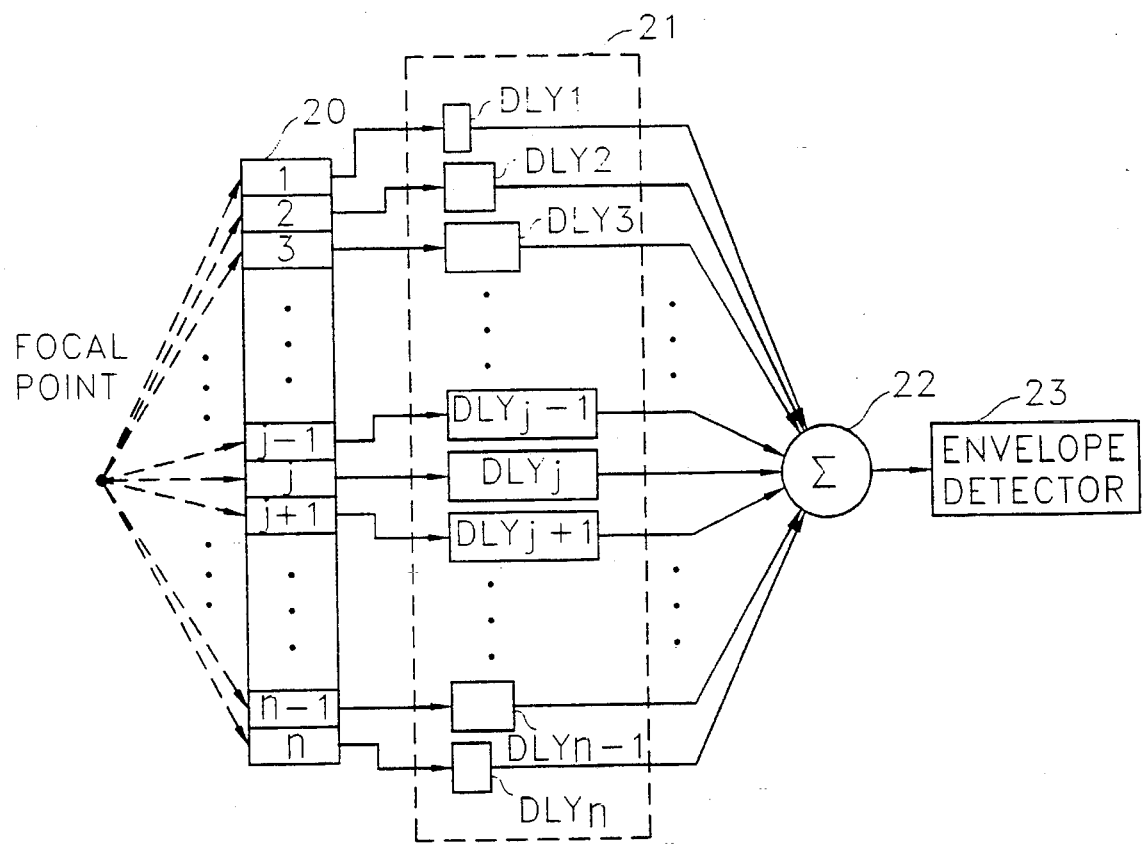
FIG. 2 is a block diagram illustrating one embodiment of a conventional receiving focusing device of an ultrasonic signal.
Figure 3:
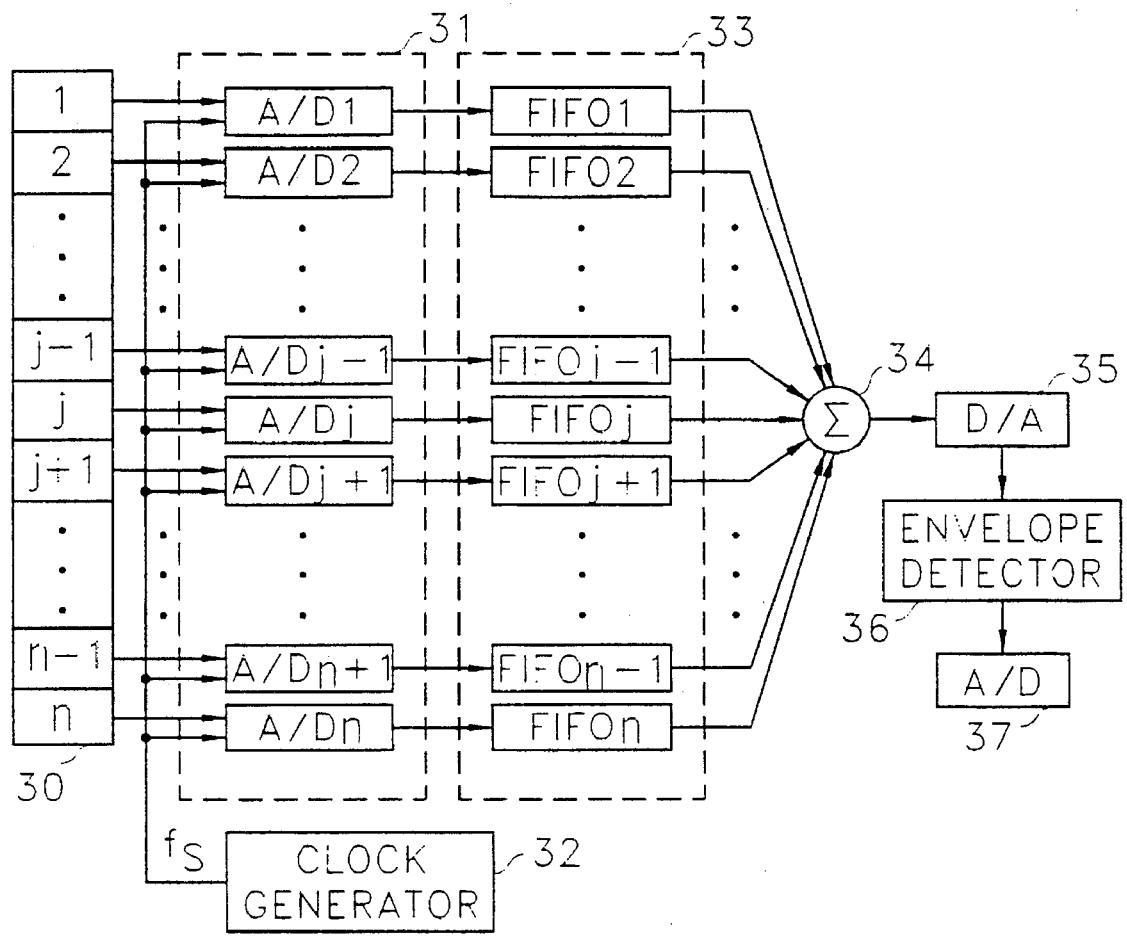
FIG. 3 is a block diagram illustrating another embodiment of a conventional receiving focusing device of an ultrasonic signal.
Figure 5:
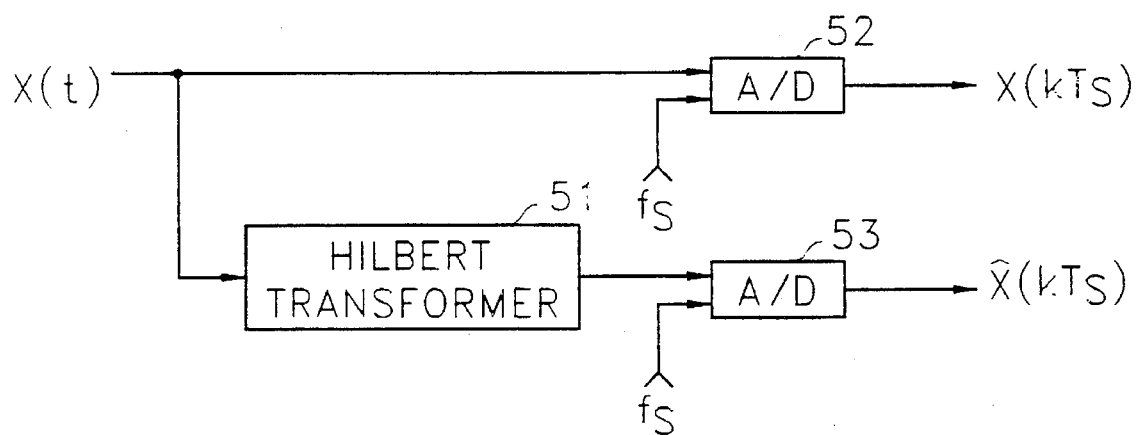
FIG. 5 is a conceptual diagram for illustrating a part of the system of FIG. 4.

FIG. 5 illustrates one of phase transformers and A/D converters in the system of FIG. 4. The system of FIG. 5 embodies an analytic signal sampling, one of bandwidth sampling methods. An analytic signal sampling method can easily obtain a desired envelope by utilizing both Hilbert transform and A/D conversion in which a sampling frequency is beyond signal bandwidth. Prior to describing the device of FIG. 5, the analytic signal sampling method can be written as follows.

When an input signal U(t) is Hilbert-transformed and the Hilbert-transformed signal is regarded as V(t), an analytic signal $X_{A(t)}$ is, as the equation (1), represented by complex adding of the two signals.

$$X_A(t) = U(t) + jV(t) \qquad (1)$$

Generally, the Fourier transform of a signal to which the Hilbert transform may be carried out has the following characteristic.

$$F[V(t)] = \begin{cases} -jF[U(t)], & f > 0 \\ jF[U(t)], & f < 0 \end{cases} \qquad (2)$$

Due to the Fourier transform characteristic in the Hilbert transform by the equation (2), the Fourier transform of the analytic signal $X_A(t)$ of the equation (1) is as follows.

$$F[U_A(t)] = \begin{cases} 2F[U(t)], & f > 0 \\ 0, & f < 0 \end{cases} \qquad (3)$$

As shown in the equation (3), a negative frequency term in the analytic signal $X_A(t)$ is removed by Fourier transform. Accordingly, if the sampling frequency $f_s$ is maintained beyond the bandwidth of an input signal [see the equation (4)], aliasing will not come to happen.

$$fs \geq BW \qquad (4)$$

In general, since the signal U(t) can be expressed as $U(t) = A(t)\cos[\omega_o t + \phi(t)]$, frequency $\psi_v$ may be defined by:

$$\begin{aligned} Y(t) &= X_A(t)\exp(-j\omega_0 t) \\ &= p(t) + jq(t) \end{aligned} \qquad (5)$$

U(t) and V(t) from the equation (5) can be written as follows.

$$\begin{aligned} U(t) &= Re[X_A(t)] \\ &= Re[Y(t)\exp(j\omega_0 t)] \\ &= p(t)\cos\omega_0 t - q(t)\sin\omega_0 t \\ &= A_I(t)\cos\omega_0 t - A_Q(t)\sin\omega_0 t \end{aligned} \qquad (6)$$

$$\begin{aligned} V(t) &= Im[X_A(t)] \\ &= Im[Y(t)\exp(j\omega_0 t)] \\ &= q(t)\cos\omega_0 t + p(t)\sin\omega_0 t \\ &= A_Q(t)\cos\omega_0 t + A_I(t)\sin\omega_0 t \end{aligned} \qquad (7)$$

$A_I(t)$ and $A_Q(t)$ in the above equations show an inphase term and a quadrature term, respectively. Therefore, an envelope value of k sampling can be obtained by:

$$A(kT_s) = [U^2(kT_s) + V^2(kT_s)]^{1/2} \qquad (8)$$

Where, $T_s$ is a sampling period, and a reciprocal of $T_s$, i.e., a sampling frequency is good enough to be maintained only beyond the bandwidth. As shown in the equation (8), it is demonstrated that the envelope detection is possible by the analytic signal sampling method. FIG. 5 illustrates a procedure that an output signal U(t) from one transducer element is supplied to a phase transformer 41A. A Hilbert transformer 51 included in the phase transformer 41A Hilbert-transforms the input signal U(t) and generates a signal V(t). The signal U(t) and the signal V(t) output from the phase transformer 41A are separately provided to a first A/D converter 52 and a second A/D converter 53. The first and second A/D converters 52 and 53 sample the input signals into a sampling frequency satisfactory to the above equation (4). Accordingly, the output signals of the first and second A/D converters 52 and 53 respectively become signals $U(kT_s)$ and $V(kT_s)$ represented by the equations (6) and (7), wherein $kT_s$ of the signal means k sampling.

The system of FIG. 4 shows that an analytic signal sampling method is applied to an ultrasonic signal focusing. Referring to FIG. 4, the array transducer 40 transforms a plurality of reflected and received ultrasonic signals into electric signals. Then, the ultrasonic signal provided to "j" transducer element of the array transducer 40 needs different delay time according to positions of the transducer elements. The signal U(t) expressed by the equation (6) can be denoted as the equation (9) including delay time.

$$U_j(t-\tau_j) = A_{jl}(t-\tau_j)\cos \omega_o(t-\tau_j) - A_{jQ}(t-\tau_j)\sin \omega_o(t-\tau_j) \qquad (9)$$

"$\tau_j$" in the equation (9) means delay time corresponding to a signal to be input into the "j" transducer element. The signal of $U_j(t-\tau_j)$ represented as the equation (9) has a quadrature difference by the array transducer 41, that is, the signal becomes a Hilbert-transformed signal of $V_j(t-\tau_j)$.

$$V_j(t-\tau_j) = A_{jQ}(t-\tau_j)\cos \omega_o(t-\tau_j) + A_{jl}(t-\tau_j)\sin\omega_o(t-\tau_j) \qquad (10)$$

The case that the signals of $U_j(t-\tau_j)$ and $V_j(t-\tau_j)$ represented by the equations (9) and (10) are applied to a focusing method using a conventional analog delayer is as follows.

$$U_j(\tau_j+d_{jk}) = A_{jl}(t-\tau_j+d_{jk}))\cos\omega_o(t-(\tau_j+d_{jk})) - A_{jQ}(t-(\tau_j+d_{jk}))\sin\omega_o(t-(\tau_j+d_{jk})) \qquad (11)$$

$$V_j(t-(\tau j+djk)) = A_{jQ}(t-\tau_j+d_{jk}))\cos\omega_o(t-(\tau+d_{jk})) + A_{jl}(t-(\tau_j d_{jk}))\sin\omega_o(t-(\tau_j+d_{jk})) \qquad (12)$$

In the equations (11) and (12), "$d_{jk}$" means delay time so that the signal corresponding to the "j" transducer element can be focused on "k" focal point. Accordingly, "$d_{jk}$" should be determined so that "$\tau_j + d_{jk}$" term may be constant to all of transducer elements. "k" sampling data obtained by the A/D converting unit 42 will be indicated by the equations (13) and (14).

$$\begin{aligned} U_{jk} &= U_j(kT_s - (\tau_j + d_{jk})) \\ &= U_j(t - \tau_j)\delta(t - (kT_s - d_{jk})) \end{aligned} \qquad (13)$$

$$V_{jk} = V_j(kT_s - (\tau_j + d_{jk})) = V_j(t-\tau_j)\delta(t-(kT_s-d_{jk})) \qquad (14)$$

Where, the data of "$U_{jk}$" and "$V_{jk}$" is "k" sampling data, "$T_s$" is a sampling period, and "$\delta(t)$" is Dirac-delta function. Then, a reciprocal of "$T_s$", that is, a sampling frequency should be maintained beyond the bandwidth of an input signal. Here, "$\delta(t-(kT_s-d_{jk}))$" is set as a variable sampling clock necessary to a digital focusing method of the ultrasonic signal. The first clock generator 43 generates variable sampling clocks suitable for delay time varying according to focal points. As a result, the first clock generator 43 supplies different sampling time to pairs of A/D converters corresponding to each of the transducer elements, in order to compensate for the differences of delay time in signals supplied to each of the transducer elements. The signals of $U_{jk}$ and $V_{jk}$ sampled by the A/D converting unit 42 are supplied to the memory unit 44. When initial data with respect to a particular focal point is supplied to the memory unit 44, the memory unit 44 stores the input data until the maximum delay time to the focal point goes by. After the lapse of the maximum delay time, the memory unit 44 outputs, in order, the stored data to an adding unit 45. The adding unit 45 adds and outputs the input data. The signals of $U_k$ and $V_k$ focused on "k" focal point by a first adder 46 and a second adder 47 are represented by the equations (15) and (16).

$$U_k = \Sigma U_{jk} = \cos\omega_o(kT_s-(\tau_j+d_{jk}))\Sigma A_{jl}(kT_s-(\tau_j d)_{jk})) - \sin\omega_o(kT_s-(\tau_j+$$

$$d_{jk}))\Sigma A_{jQ}(kT_s-(\tau_j d_{jk})) \quad (15)$$

$$V_k \Sigma V_{jk} = \cos\omega_o(kT_s-(\tau_j+d_{jk}))\Sigma a_{jQ}(kT_s-(\tau_j+d_{jk}))+\sin\omega_o(kT_s-(\tau_j+d_{jk}))\Sigma A_{jl}(kT_s-(\tau_j+d_{jk})) \quad (16)$$

Where, "$U_k$" is a focusing signal of "k" focal point added in the first adder 46, "$V_k$" is a focusing signal of "k" focal point added in the second adder 47. A first envelope detector 48 calculates the signals added in the adding unit 45 by the equation (17) and generates envelope data $A_k$ with the result of calculation.

$$\begin{aligned} A_k &= (U_k^2 + V_k^2)^{1/2} \quad (17)\\ &= [\Sigma A_{jl}(kT_s - (\tau_j + d_{jk}))^2 + \\ &\quad \Sigma A_{jQ}(kT_s - (\tau_j + d_{jk}))^2]^{1/2} \end{aligned}$$

Since envelope data means amplitude of a signal, the equation (17) corresponds to the envelope data of "k" focal point.

Figure 6:
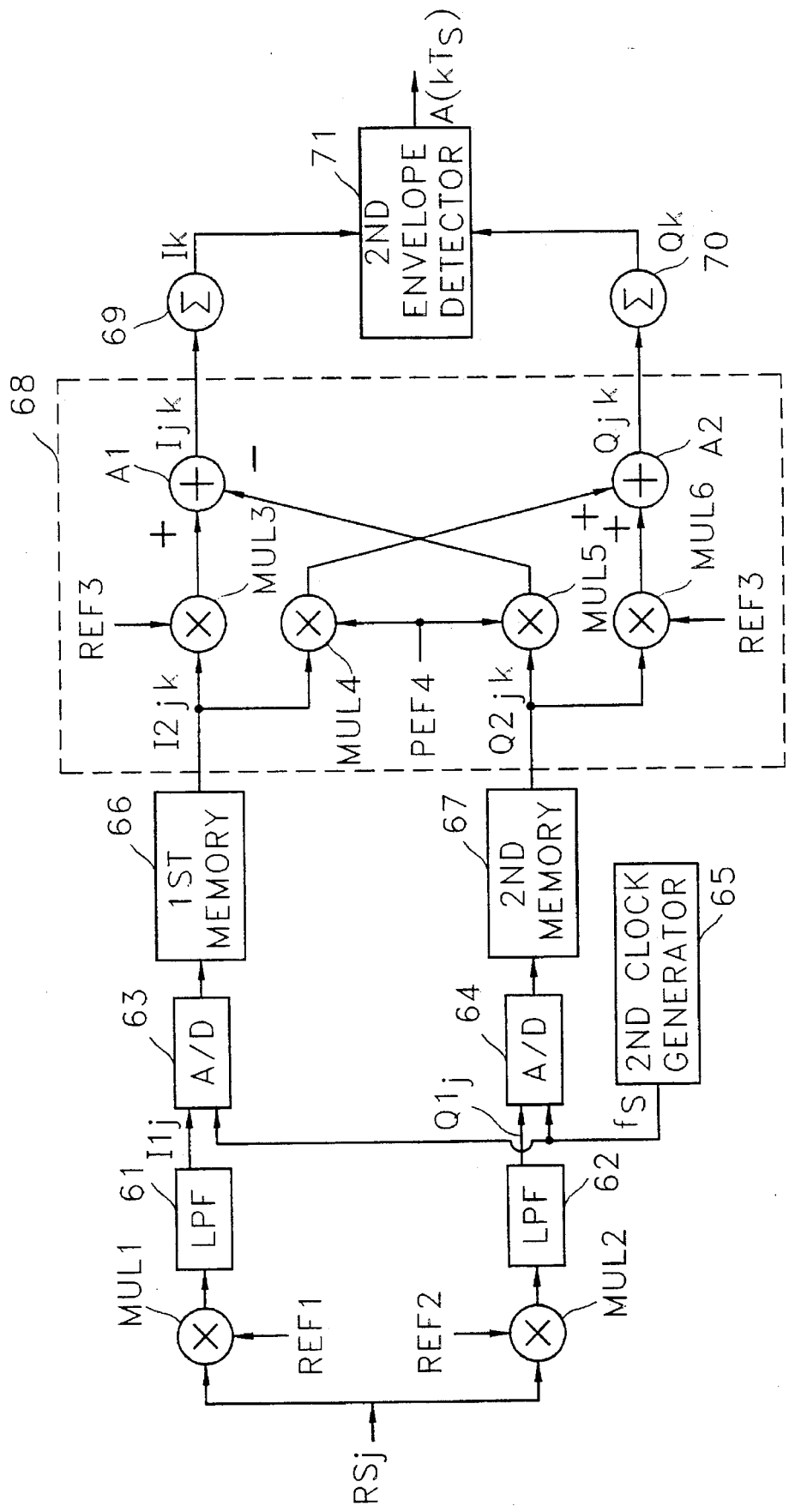
FIG. 6 is a block diagram illustrating another preferred embodiment of an ultrasonic imaging system for focusing a digital signal in accordance with the present invention.

FIG. 6 illustrates another preferred embodiment of an ultrasonic imaging system for focusing a digital signal in accordance with the present invention. FIG. 6, like FIG. 4, relates to a focusing system of an ultrasonic signal received through an array transducer (not shown) composed of n transducer elements in numbers. The system of FIG. 6 shows only the focusing of an ultrasonic signal being input through any one of transducer elements because the same procedure for focusing may be applied to each of n ultrasonic signals transformed into electric signals. The system of FIG. 6 includes a frequency band transformer composed of a multiplier 61 or 62 and low pass filter 63 or 64. In addition, first and second A/D converters 65 and 66, and a clock generator 67 form a delayed-time difference eliminator. An output signal ($U_j$) of the "j" transducer element is supplied to the first multiplier 61 and the second multiplier 62. Either first multiplier 61 or second multiplier 62 multiplies an output signal of the transducer element with a first reference signal REF1 or a second reference signal REF2, and supplies the multiplied value to a first low pass filter 63 or a second low pass filter 64. Output terminals of the first and second low pass filters 63 and 64 are connected to input terminals of the first and second A/D converters 65 and 66, respectively. The first and second A/D converters 65 and 66 convert the input signal into a digital signal according to a sampling frequency $f_s$ supplied from the clock generator 67, and outputs the converted signal to first and second memories 68 and 69. The first and second memories 68 and 69 store the output from the A/D converter, and output the stored data. A phase compensator 70 includes third through sixth multipliers 710–716 which multiply the output signal from the first and second memories 68 and 69 by a third reference signal REF3 or a fourth reference signal REF4, a subtracter 718 which subtracts the output of a third multiplier 714 from that of a third multiplier 710, and a first adder 720 which adds the output of fourth and sixth multipliers 712 and 716. The output of the phase compensator 70 is supplied to second and third adders 71 and 72. The second and third adders 71 and 72 sum output signals of all the phase compensators corresponding to a predetermined number of transducer elements (not shown), and supply the summed value to envelope detector 73.

Such a preferred embodiment of FIG. 6 relates to the focusing system of an ultrasonic signal using a quadrature sampling method, one of bandwidth sampling methods, and the operation will be described in detail. The quadrature sampling method moves reflected ultrasonic signals from radio frequency (RF) band to baseband using a predetermined number of multipliers and low pass filters, and samples them. Accordingly, it is advantageous that the envelope of reflected ultrasonic signals can be easily obtained if a sampling frequency comes to be maintained beyond the bandwidth of reflected ultrasonic signals. First, the ultrasonic signal U(t) received from the transducer element is represented by the equation (18).

$$\begin{aligned} U(t) &= A(t)\cos(\omega_0 t + \theta(t)) \quad (18)\\ &= A_I(t)\cos\omega_0 t - A_Q(t)\sin\omega_0 t \end{aligned}$$

Where, $A_I(t)$ is an inphase term of the signal U(t), and $A_Q(t)$ is a quadrature term of X(t). Accordingly, from the equation (18) an ultrasonic signal $U_j(t)$ supplied to the "j" transducer element of the array transducer 40 is represented below.

$$\begin{aligned} U_j(t-\tau_j) &= A_j(t-\tau_j)\cos(\omega_0(t-\tau_j) + \theta(t-\tau_j)) \quad (19)\\ &= A_{jl}(t-\tau_j)\cos\omega_0(t-\tau_j) - A_{jQ}(t-\tau_j)\sin\omega_0(t-\tau_j) \end{aligned}$$

Here, "$\tau_j$" means delay time of the "j" transducer element of transducer elements being in the middle of the array transducer. Such a reflected ultrasonic signal $U_j$ is supplied to the first multiply 61 and multiplied by a first reference signal REF1 of "$\cos\omega_r t$", and at the same time is supplied to the second multiplier 62 and multiplied by a second reference signal REF2 of "$\sin\omega_r t$". Here, "$\omega_r$" is a reference frequency utilizing in the first and second multipliers 61 and 62. The signals, which are multiplied by each of reference signals in the first and second multipliers 61 and 62, have no high frequency components through the first and second low pass filters 63 and 64, and are expressed by the equations (20) and (21).

$$\begin{aligned} Il_j &= U_j(t-\tau_i)\cos\omega_r t|_{LPF} \quad (20)\\ &= \frac{1}{2} A_{jl}(t-\tau_j)\cos[(\omega_0 - \omega_r)t - \omega_0\tau_j] - \\ &\quad \frac{1}{2} A_{jQ}(t-\tau_j)\sin[(\omega_0 - \omega r)t - \omega_0\tau_j] \end{aligned}$$

$$\begin{aligned} Q1_j &= X_j(t-\tau_i)\sin\omega_r t|_{LPF} \quad (21)\\ &= \frac{1}{2} A_{jl}(t-\tau_j)\sin[(\omega_0 - \omega_r)t - \omega_0\tau_j] - \\ &\quad \frac{1}{2} A_{jQ}(t-\tau_j)\cos[(\omega_0 - \omega r)t - \omega_0\tau_j] \end{aligned}$$

Where, high frequency components, that is, an frequency addition term of "$(\omega_0+\omega_r)t$" is removed. Consequently, the signal passing through the multiplier 61 or 62 and the low pass filter 63 or 64 is moved from RF band to baseband. The two signals ($Il_j, Q1_j$) represented by the equations (20) and (21) are separately supplied to the first and second A/D converters 65 and 66. The first and second A/D converters 65 and 66 sample the input signal according to the sampling frequency $f_s$ supplied from the clock generator 67. The clock generator 67 generates a sampling clock of the sampling frequency $f_s$ more than the bandwidth of reflected and received ultrasonic signals. The clock generator 67, like the clock generator 43 of FIG. 4, supplies different sampling time with each other to pairs of A/D converters corresponding to each of the transducer elements, in order to compensate for the differences of delay time in the signals supplied to each of the transducer elements. Therefore, pairs of A/D converters corresponding to each of the transducer elements output the digital signals in which the differences of the delay time occurring between signals received from the array transducer are compensated. The first and second A/D converters 65 and 66 output the digital signals obtained through sampling to the first and second memories 68 and 69. Memories (not shown) corresponding to other transducer elements as well as the memories 68 and 69 corresponding to the "j" transducer element, in the case that initial data with respect to a particular focal point is input therein, store the input data until the maximum delay time of the focal point goes by. After the lapse of the maximum delay time, the memories output, in order, the stored data to the adding unit 45. A signal $I2_{jk}$ supplied from the first memory 68 to the third and fourth multipliers 710 and 712, and a signal $Q2_{jk}$ supplied from the second memory 69 to the fifth and sixth multipliers 714 and 716 are as follows.

$$I2_{jk} = \frac{1}{2} A_{jI}[kT_s - (\tau_j - m_{jk}T_s)]\cos[(\omega_0 - \omega_r)kT_s - \omega_0(\tau_j - m_{jk}T_s) - \omega_r m_{jk}T_s] - \frac{1}{2} A_{jQ}[kT_s - (\tau_j - m_{jk}T_s)]\sin[(\omega_0 - \omega_r)kT_s - \omega_0(\tau_j - m_{jk}T_s) - \omega_r m_{jk}T_s] \quad (22)$$

$$Q2_{jk} = \frac{1}{2} A_{jI}[kT_s - (\tau_j - m_{jk}T_s)]\sin[(\omega_0 - \omega_r)kT_s - \omega_0(\tau_j - m_{jk}T_s) - \omega_r m_{jk}T_s] - \frac{1}{2} A_{jQ}[kT_s - (\tau_j - m_{jk}T_s)]\cos[(\omega_0 - \omega_r)kT_s - \omega_0(\tau_j - m_{jk}T_s) - \omega_r m_{jk}T_s] \quad (23)$$

Where, "k" shows "k" sampling position, "$T_s$" is a sampling period, and "$m_{jk}$" is the difference between the "j" transducer element and the middle transducer elements with the shortest delay time. Therefore, the "$m_{jk}$" should be selected to be "$m_{jk}T_s \approx \tau_j$". Envelope data is compensated from the differences between delay times by adding either a signal $I_k$ or a signal $Q_k$ with respect to all the transducer elements in order to obtain envelope data at "k" focal point. However, since "$\omega_r m_{jk}T_s$" included in phase terms has differently "$m_{jk}$" per all the transducer elements, errors by phase difference may happen. In order to solve the problem, the present invention includes the phase compensator 70, connected between memories and adders, for compensating phase errors. First, the equations (22) and (23) can be simply represented as follows.

$$B_{jI}(k) = \frac{1}{2} A_{jI}[kT_s - (\tau_j - m_{jk}T_s)] \quad (24)$$

$$B_{jQ}(k) = \frac{1}{2} A_{jQ}[kT_s - (\tau_j - m_{jk}T_s)] \quad (25)$$

$$\theta = (\omega_0 - \omega_r)kT_s - \omega_0(\tau_j - m_{jk}T_s) \quad (26)$$

$$\psi_{jk} = -\omega_r m_{jk}T_s \quad (27)$$

The equations (22) and (23) can be indicated as follows using the equations (24) through (27).

$$I2_{jk} = B_{jI}(k)\cos(\theta + \psi_{jk}) - B_{jQ}(k)\sin(\theta + \psi_{jk}) \quad (28)$$

$$Q2_{jk} = -B_{jI}(k)\sin(\theta + \psi_{jk}) - B_{jQ}(k)\cos(\theta + \psi_{jk}) \quad (29)$$

In "$\psi_{jk} = -\omega_r m_{jk}T_s$" utilized for the phase compensation, since "$\omega_r$" and "$T_s$" are known values, "$m_{jk}$" is a variable according to focal points but can be anticipated, and "$\psi_{jk}$" can be calculated by previously known values ($\omega_r$, $T_s$, $m_{jk}$). Accordingly, the phase, compensation is possible by using a "$\psi_{jk}$" value added to the third and fourth reference signals REF3 and REF4 which are supplied to the third to sixth multipliers 710~716. The third multiplier 710 multiplies a signal $I2_{jk}$ supplied from the frist memory 68 and the third reference signal REF3 of "$\cos\psi_{jk}$", and outputs the multiplied value to a subtracter 718. The fourth multiplier 712 multiplies the signal $I2_{jk}$ supplied from the frist memory 68 and the fourth reference signal REF4 of "$\sin\psi_{jk}$", and outputs the multiplied value to a first adder 720. The fifth multiplier 14 multiplies a signal $Q2_{jk}$ supplied from the second memory 69 and the fourth reference signal REF4 of "$\sin\psi_{jk}$", and outputs the multiplied value to the subtracter 718. The sixth multiplier 716 multiplies the signal $Q2_{jk}$ supplied from the second memory 69 and the third reference signal REF3 of "$\cos\psi_{jk}$", and outputs the multiplied value to the first adder 720. The subtracter 718 subtracts an output signal of the fifth multiplier 714 from an output singal of the third multiplier 710, and outputs the subtracted value to the second adder 71. The first adder 720 adds output signals of the fourth and sixth multipliers 712 and 716, and outputs the added value to the third adder 72. Then, the output signals $I_{jk}$ and $Q_{jk}$ of the subtracter 718 and third adder 720 have no the phase errors $\psi_{jk}$ by means of the computation of third to sixth multipliers 710~716, subtracter 718 and first adder 720, which is represented by the following equations.

$$\begin{aligned} I_{jk} &= I2_{jk}\cos\psi_{jk} - Q2_{jk}\sin\psi_{jk} \\ &= B_{jI}(k)\cos\theta - B_{jQ}(k)\sin\theta \end{aligned} \quad (30)$$

$$\begin{aligned} Q_{jk} &= I2_{jk}\sin\psi_{jk} - Q2_{jk}\cos\psi_{jk} \\ &= -B_{jI}(k)\sin\theta - B_{jQ}(k)\cos\theta \end{aligned} \quad (31)$$

The signals in which phase errors are removed by the phase compensator 70 are added to each of output singals of phase compensators (not shown) corresponding to other transducer elements in the second and third adders 71 and 72, and are focused as follows.

$$I_k = \sum_j I_{jk} \quad (32)$$

$$Q_k = \sum_j Q_{jk} \quad (33)$$

An envelope detector 73, which receives two components of inphase and quadrature focused as the equations (32) and (33), detects an envelope "$A(kT_s)$" according to the equation (34).

$$A(kT_s) = (I_k^2 + Q_k^2)^{1/2} \quad (34)$$

The system of FIGS. 4 and 6 can be applied to synthetic focusing method as well as the above PSDF method.

As described above, a digital focusing method and system in accordance with the present invention, even if an ultrasonic signal is focused by the digital method, solves a high sampling frequency and the difficulty of envelope detection in a digital process, using both analytic signal sampling and quadrature sampling among bandwidth sampling methods. The present invention reduces complexity of a focusing system and makes dynamic focusing possible, and thereby has an effect on easiness of the envelope detection.

What is claimed is:

1. An ultrasonic imaging system which focuses ultrasonic signals reflected from an object on at least one focal point according to a receiving focusing method, the system comprising:

a plurality of transducer elements for respectively receiving said ultrasonic signals relating to said at least one focal point and generating analog signals corresponding to said ultrasonic signals, said analog signals having a frequency band;

a plurality of frequency band transformers, coupled to each of said transducer elements, for respectively receiving and transforming the frequency band of said analog signals received from said transducer elements, each of said frequency band transformers comprising a multiplier and a low pass filter; each of said transducer elements being coupled to at least two said frequency band transformers;

a plurality of delayed-time difference eliminators, coupled to said frequency band transformers, for eliminating the difference of delay times due to varying positions of focal points and for performing analog to digital conversion, said delayed-time difference eliminators comprising a sampling clock for generating a higher frequency than the frequency bandwidth of an analog signal transformed by a frequency band transformer to which the sampling clock is coupled; each of said delayed-time difference eliminators comprising a first A/D converter and a second A/D converter; each of said A/D converters being coupled to a frequency band transformer;

a plurality of memories, connected to said delayed-time difference eliminators for storing digital signals output from said delayed-time difference eliminators;

a plurality of phase compensators, connected to said plurality of memories, for compensating phase errors in digital signals output from said memories and included in a first digital signal and a second digital signal, said first digital signal being generated by said first A/D converter and said second digital signal being generated by said second A/D converter, said phase compensators containing a plurality of multipliers, to carry out quadrature sampling phase-error-elimination;

a plurality of adders coupled to said plurality of phase compensators for adding output signals of said phase compensators; and an envelope detector for detecting envelope data from output signals of said plurality of adders.

2. The ultrasonic imaging system of claim 1 wherein each of said phase compensators comprises a first multiplier, a second multiplier, a third multiplier, a fourth multiplier, a subtracter and an adder.

3. The ultrasonic imaging system of claim 2 wherein said first multiplier is configured to multiply a signal supplied from said first A/D converter through a first memory by a first reference signal, and wherein said second multiplier is configured to multiply a signal supplied from said first A/D converter through said first memory by a second reference signal; said third multiplier is configured to multiply a signal supplied from said second A/D converter through a second memory by said second reference signal; and wherein said fourth multiplier is configured to multiply a signal supplied from said second A/D converter through said second memory by said first reference signal; and wherein said subtractor is configured to subtract an output signal of said third multiplier from an output signal of said first multiplier, and said adder is configured to add an output signal from said second multiplier with said output signal of said fourth multiplier, such that two output signals without phase errors are provided to the plurality of adders.

4. The ultrasonic imaging system of claim 1 wherein said plurality of memories are first-in-first-out memories which receive output signals of said A/D converters.

5. A method of ultrasonic imaging which focuses ultrasonic signals reflected from an object on at least one focal point and which eliminates phase errors, comprising the steps of:

reviewing ultrasonic signals reflected from an object on at least one focal point;

generating analog signals corresponding to said ultrasonic signals;

lowering the frequency bands of said analog signals;

eliminating the difference in delay times due to varying positions of focal points by converting said analog signals to digital signals using a sampling frequency supplied form a clock generator;

phase compensating the digital signals after the difference in delay times have been eliminated, by using a quadrature sampling technique;

adding the digital signals after phase compensation; and detecting envelope data of said digital signals.

6. The method of claim 5 wherein said steps of eliminating the difference in delay times and phase compensating involve the step of moving reflected ultrasonic signals from radio frequency band to baseband using a predetermined number of multipliers, low pass filters and a quadrature sampling technique.

7. The method of claim 6 further comprising the step of maintaining a sampling frequency beyond a bandwidth of the reflected ultrasonic signals.

8. The method of claim 7 wherein said step of detecting envelope data comprises the step of receiving inphase and quadrature components of the digital signals.

* * * * *

UNITED STATES PATENT AND TRADEMARK OFFICE
CERTIFICATE OF CORRECTION

PATENT NO. : 5,581,036
DATED : December 3, 1996
INVENTOR(S) : Seong H. Chang and Song B. Park It is certified that error appears in the above-indentified patent and that said Letters Patent is hereby corrected as shown below:

Column 12, line 25, delete "form" and insert therefor --from--.

Signed and Sealed this

Eleventh Day of March, 1997

Attest:

BRUCE LEHMAN

Attesting Officer

Commissioner of Patents and Trademarks